United States Patent [19]

Suguro

[11] Patent Number: 4,730,049

[45] Date of Patent: Mar. 8, 1988

[54] PROCESS FOR PREPARING 5-(2-CHLOROBENZYL)-4,5,6,7-TETRAHYDROTHIENO (3,2-C)PYRIDINE

[75] Inventor: Toshio Suguro, Kamifukuoka, Japan

[73] Assignees: Nisshin Flour Milling Co., Ltd.; Nisshin Chemicals Co., Ltd., both of Japan

[21] Appl. No.: 782,409

[22] Filed: Oct. 1, 1985

[30] Foreign Application Priority Data

Oct. 3, 1984 [JP] Japan .................. 59-206280

[51] Int. Cl.$^4$ .......................... C07D 495/04
[52] U.S. Cl. ................................. 546/114
[58] Field of Search ......................... 546/114

[56] References Cited

PUBLICATIONS

Maffrand et al., Eur. J. Med. Chem., Chimica Therapeutica, vol. 9(5), pp. 483–486 (1974).
Dehmlow et al., Phase Transfer Catalysis, Verlag Chemie, pp. 1–6 and 93–99 (1980).

*Primary Examiner*—Henry R. Jiles
*Assistant Examiner*—Bernard I. Dentz
*Attorney, Agent, or Firm*—Abelman Frayne Rezac & Schwab

[57] ABSTRACT

An improved process for the preparation of 5-(2-chlorobenzyl)-4,5,6,7-tetrahydrothieno[3,2-c]pyridine and acid addition salts thereof, which are useful as a medicine. This process comprises effecting reaction between 4,5,6,7-tetrahydrothieno[3,2-c]pyridine and 2-chlorobenzyl halide in the presence of a phase transfer catalyst.

8 Claims, No Drawings

PROCESS FOR PREPARING 5-(2-CHLOROBENZYL)-4,5,6,7-TETRAHYDROTHIENO (3,2-C)PYRIDINE

FIELD OF THE INVENTION

This invention relates to processes for preparing 5-(2-chlorobenzyl)-4,5,6,7-tetrahydrothieno[3,2-c]pyridine and acid addition salts thereof which are useful as a medicine, and more particularly to an improved process using a phase transfer catalyst.

BACKGROUND OF THE INVENTION 5-(2-Chlorobenzyl)-4,5,6,7-tetrahydrothieno[3,2-c]pyridine prepared by the present invention has the following formula (I) and is generally termed Ticlopidine.

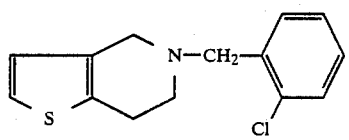
(I)

Ticlopidine is a compound known, per se, and its pharmacological effects are disclosed in EUR. J. MED. CHEM.-CHIMICA THERAPEUTICA, SEPTEMBER-OCTOBER 1974-9, No. 5, p 487. Because of their anti-inflammatory, vasodilative and platelet agglutination inhibiting activities, in particular, Ticlopidine and its salts are useful as medicines.

The synthetic route of Ticlopidine by reacting 4,5,6,7-tetrahydrothieno[3,2-c]pyridine of the formula (II)

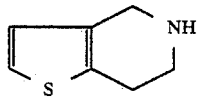
(II)

with 2-chlorobenzyl halide of the formula (III)

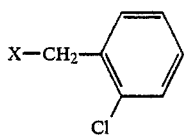
(III)

wherein X represents Cl, Br or I, has heretofore been known, as disclosed in EUR. J. MED. CHEM.-CHIMICA THERAPEUTICA, SEPTEMBER-OCTOBER 1974-9, No. 5, p 483. In this process, the compound of the formula (II) and the compound of the formula (III) are heated under reflux in ethyl alcohol in the presence of potassium carbonate. The process, however, has such disadvantages that the reaction proceeds rigorously to a considerable extent with the formation of much by-products, and that the subsequent purification of the reaction mixture is complicated and moreover, this reaction gives the desired product in yield as low as about 25%. As an alternative to the above-mentioned process, the aforesaid literature discloses a process (reaction route A as mentioned below) wherein thieno[3,2-c]pyridine is N-benzylated with 2-chlorobenzyl halide of the formula (III) to the corresponding quaternary ammonium salt, followed by reduction with NaBH4, or a process (reaction route B as mentioned below) wherein 4,5,6,7-tetrahydrothieno[3,2-c]pyridine of the formula (II) is reacted with a highly active 2-chlorobenzoic acid halide, followed by reduction with LiAlH4. These alternatives, however, have the disadvantages of increased process steps and troublesomeness of manufacture:

Reaction route A

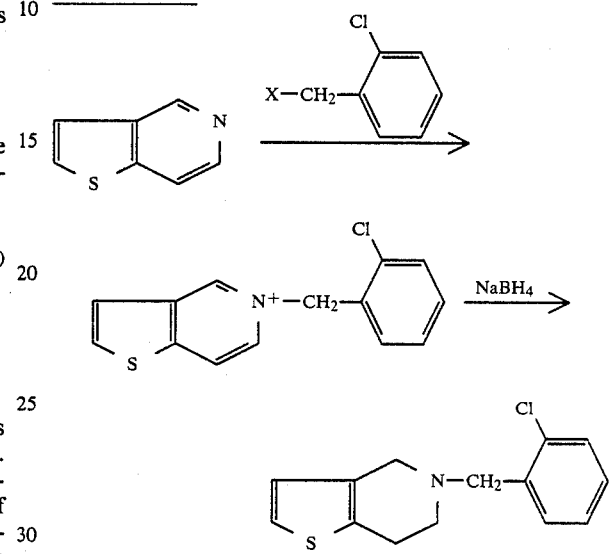

Reaction route B

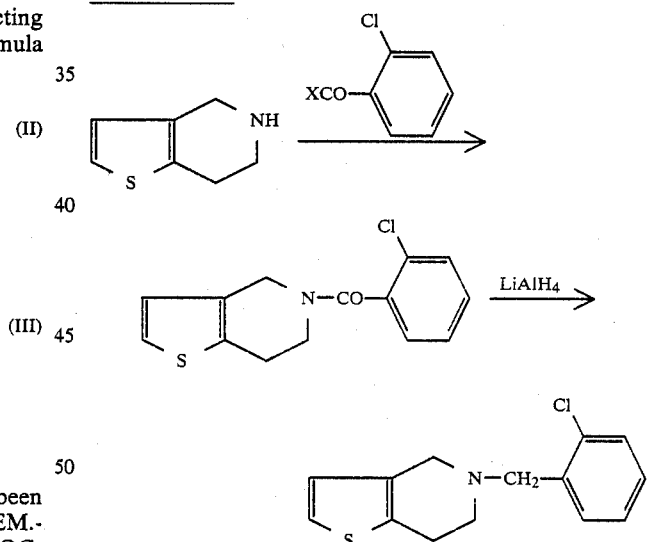

SUMMARY OF THE INVENTION

A principal object of the invention is to provide an improved process for preparing 5-(2-chlorobenzyl)-4,5,6,7-tetrahydrothieno [3,2-c]pyridine and acid addition salts thereof in high yields and in an economical way.

Other objects of the invention will become apparent from the following detailed description.

As a result of extensive studies conducted with the view of accomplishing the above-mentioned objects, the present inventor has been successful in sharply increasing the yield of product resulting from N-benzylation of 4,5,6,7-tetrahydrothieno[3,2-c]pyridine by a simple and easy process wherein the N-benzylation is effected under mild conditions using a phase transfer catalyst.

In accordance with the present invention, the compound of the formula (I) can be prepared by reacting the compound of the formula (II)

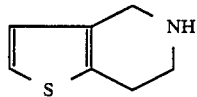
(II)

with the compound of the formula (III)

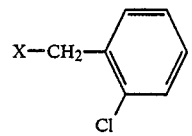
(III)

wherein X represents Cl, Br or I, in the presence of a phase transfer catalyst.

The compound of the formula (I) may be isolated from the reaction product in a free state or in the form of salt. Accordingly, the present invention includes also a process for preparing acid addition salts of the compound of the formula (I) with inorganic or organic acids.

DESCRIPTION OF PREFERRED EMBODIMENTS

In general, phase transfer catalysts perform catalysis under mild conditions. For instance, where quaternary ammonium or phosphonium salts are used as catalysts, the catalysts function in the following manner. In the reaction system, there are two phases which are immiscible with each other, one of which (usually an aqueous phase) contains salts which act as bases or nucleophilic agents, and the other of which (an organic phase) contains organic substrates which react with the above-mentioned salts. Since the phase containing the salts does not dissolve in the phase containing the organic substrates, no reaction takes place if nothing happens in the interface. Under such circumstances, when quaternary ammonium or phosphonium, or halides or hydrogen sulfate (propably sulfate) thereof is added as a phase transfer catalyst, forming a lipophilic cation in a solution, this cation dissolves not only in the aqueous phase but also in the organic phase and contacts with the salts in the aqueous phase to exchange its own anion for the anions present in excess in the aqueous solution. Such anion exchange is represented by the following equation.

$$Q^+X^-(aq) + M^+Nu^-(aq) \rightleftharpoons Q^+Nu^{-(aq)} + M^+X^-(aq)$$

wherein $Q^+$ stands for a quaternary cation, $X^-$ does an anion, $M^+$ does a metal cation, and $Nu^-$ does a nucleophile. The desired reaction cannot take place if only anion exchange provides completed reaction. Now, the anion which is capable of acting as a nucleophilic agent forms together with $Q^+$ an ion pair and must transfer into the organic phase. Accordingly, the condition under which a phase transfer catalyst can function favorably is a second equilibrium, i.e., a phase transfer equilibrium, which is represented by the following equation.

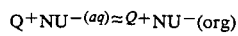

When a nucleophilic agent or a base (both are represented by Nu for convenience's sake) enters once the nonpolar (organic) phase, substitution reaction or deprotonation (elimination reaction) takes place to form a reaction product. In the nucleophilic substitution reaction, $Q^+$ eventually forms together with a leaving group an ion pair. If the leaving group is $X^-$, an ion pair QX forms, which ion pair enters the above-mentioned equilibrium. Such phase transfer catalysis cycle is as schematically illustrated below.

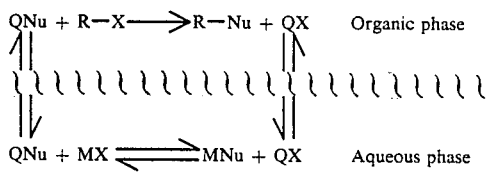

The present invention consists in applying such phase-transfer catalysis to organic synthesis. The phase transfer catalysts include quaternary ammonium salts such as trimethylbenzyl ammonium hydroxide, hydrogen sulfate tetra-n-butyl ammonium, trioctylmethyl ammonium chloride, and triethylbenzyl ammonium chloride; phosphonium salts such as tetrabutyl phosphonium chloride; and crown ethers such as 18-crown-6 and dibenzo 18-crown-6.

In industrial scale, the above-mentioned reaction using a phase transfer catalyst is usually carried out in an aqueous-organic two-phase system in the presence of a base. The bases include sodium hydroxide, potassium hydroxide, lithium hydroxide, potassium carbonate, sodium carbonate, etc. Of these bases, preferable is sodium hydroxide becasue it is inexpensive and easy to use.

Furthermore, organic solvents which constitute the aqueous-organic two-phase system may be any solvents so long as they are immiscible with water. Representative of the organic solvents includes hydrocarbons such as benzene, toluene and xylene; ethers such as isopropyl ether and diethyl ether; and alcohols of $C_3$ or more such as isopropanol and n-butanol. From the standpoint of economy and solubility with reaction product, benzene type solvents are preferred.

In the reaction, the base mostly dissolves in an aqueous phase of the reaction system. A concentration of the base in the aqueous phase is usually about 2.5–5.0 moles, but not limited thereto. Water and an organic solvent may be used in any proportions if an aqueous-organic two-phase system is formed thereby, for instance, when a benzene type solvent is used, the proportion of water to the organic solvent is from 7:3 to 3:7, preferably 5:5. Since the process of the present invention is carried out under mild conditions, the reaction is advantageously effected at about room temperature. The reaction time is usually 24–48 hours, though it is depending on the reaction temperature and the molar ratio of the compound of the formula (III) to that of the formula (II). The amount of the compound of the formula (III) based on that of the formula (II) may be favorable if it is greater than the equimolar amount, though the greater the amount of the compound of the formula (III), the quicker the completion of the reaction. The catalyst is usually used in an amount equivalent to about 0.01-0.05 based on the compound of the formula (II), thereby giving the end compound of the formula (I) in good yields.

Furthermore, when phosphonium salts or crown ethers are used as phase transfer catalysts, the above-mentioned reaction proceeds even in an organic single phase system.

The salts of the compound of the formula (I) may be formed by the method well known to those skilled in the art.

This invention is further illustrated by the following examples, but not limited thereto

EXAMPLE 1

To a solution of 4,5,6,7-tetrahydrothieno[3,2-c]pyridine hydrochloride (580 mg, 3.3 mmol) and 2-chlorobenzyl chloride (640 mg, 3.9 mmol) in benzene (5.0 ml) were added an aqueous 5M NaOH solution (5 ml), and trimethylbenzyl ammonium hydroxide (100 mg of 40% methanol solution). The mixture was stirred for 40 hours at room temperature. The reaction mixture was allowed to stand, thereby separating an aqueous layer from an organic layer The organic layer was washed with water and then with saturated NaCl solution, dried (over MgSO4) and concentrated. The residue was purified by silica gel column chromatography to prepare 650 mg (yield 74.7%) of 5-(2-chlorobenzyl)-4,5,6,7-tetrahydrothieno[3,2-c]pyridine as an oily product, b.p. 155.0°-158.0° C. (1.5 mmHg). This pyridine was dissolved in hydrogen chloride saturated ethyl alcohol (5 ml) and the solution was then concentrated and cooled. The precipitated hydrochloride was filtered off and dried. The yield 420 mg (42.4%), m.p. 190° C.

Mass analysis: (70eV,M/Z) 265, 263(M+), 125, 110.
IR (KBr): 2300 cm$^{-1}$ (broad, hydrochloride).

EXAMPLE 2

To a solution of 4,5,6,7-tetrahydrothieno-[3,2-c,]pyridine hydrochloride (480 mg, 2.74 mmol) and 2-chlorobenzyl chloride (528 mg, 1.2 times mol) in benzene (5 ml) were added an aqueous 5M NaOH solution (5 ml) and then trioctylmethyl ammonium chloride (20 mg). The mixture was stirred for 40 hours at room temperature. The same subsequent procedure as in Example 1 gave 540 mg (yield 74.9%) of 5-(2-chlorobenzyl,-4,5,6,7-tetrahydrothieno[3,2-c]-pyridine hydrochloride, m.p 190° C.

EXAMPLE 3

To a solution of 4,5,6,7-tetrahydrothieno-[3,2-c]pyridine hydrochloride (24.0 g, 0.137 mol) and 2-chlorobenzyl chloride (26.4 g, 0.164 mol) in benzene (100 ml) were added an aqueous 2.5N NaOH solution (150 ml, 0.375 mol) and tetra-n-butyl ammonium hydrogen sulfate (1.0 g, 0.003 mol). The mixture was stirred for 40 hours at toom temperature. The reaction mixture was allowed to stand, thereby separating an organic layer from an aqueous layer. The aqueous layer was extracted with benzene (100 ml×2 times). The originally separated organic layer was combined with the extracted benzene layer, and the combined organic layer was washed with water and then with saturated NaCl solution, dried (over K2CO3), and concentrated. The residue was distilled under reduced pressure to prepare 28,8 g (yield 80.0%) of 5-(2-chlorobenzyl)-4,5,6,7tetrahydrothieno[3,2-c]pyridine as an oily product, b.p. 155.0°-158.0° C. (1.5 mmHg).

The same procedure as in Example 1 gave the hydrochloride. The yield, 26.1 g (63.5%).

What is claimed is:

1. A process for preparing 5-(2chlorobenzyl)-4,5,6,7-tetrahydrothieno[3,2-c]pyridine of the formula (I)

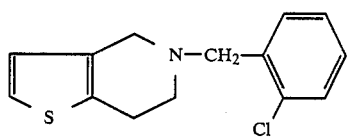

and acid addition salts thereof, which comprises reacting a compound of the formula (II)

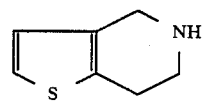

with a compound of the formula (III)

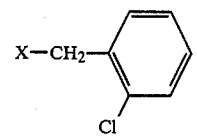

wherein X represents Cl, Br or I, in the presence of a phase transfer catalyst and a base.

2. The process of claim 1 wherein the phase transfer catalyst is selected from the group consisting of quaternary ammonium salts, phosphonium salts or crown ethers.

3. The process of claim 2 wherein the quaternary ammonium salts are trimethylbenzyl ammonium hydroxide, hydrogen sulfate tetra-n-butyl ammonium, trioctylmethyl ammonium chloride or triethylbenzyl ammonium chloride.

4. The process of claim 1 wherein the catalyst is used in the equivalent of 0.01-0.05 based on the compound of the formula (II).

5. The process of according to claim 1 wherein the reaction is conducted at room temperature.

6. The process of claim 2 wherein the reaction is conducted at room temperature.

7. The process of claim 3, wherein the reaction is conducted at room temperature.

8. The process of claim 4, wherein the reaction is conducted at room temperature.

* * * * *